United States Patent [19]

Sato et al.

[11] Patent Number: 4,818,761
[45] Date of Patent: * Apr. 4, 1989

[54] 2-(4-PYRIDYLAMINOMETHYL)-BENZIMIDAZOLE DERIVATIVES HAVING ANTIVIRAL ACTIVITY

[75] Inventors: Nobukatsu Sato, Nara; Haruo Kuriyama, Mukoh; Masanobu Agoh, Ikeda, all of Japan

[73] Assignee: Maruishi Seiyaku Kabushiki Kaisha, Osaka, Japan

[ * ] Notice: The portion of the term of this patent subsequent to Dec. 22, 2004 has been disclaimed.

[21] Appl. No.: 71,251

[22] Filed: Jul. 8, 1987

[30] Foreign Application Priority Data

Jul. 11, 1986 [JP] Japan ................................. 61-164324
Jan. 21, 1987 [JP] Japan ................................. 62-13258

[51] Int. Cl.⁴ .......................................... C07D 401/02
[52] U.S. Cl. ..................................... 514/341; 546/271
[58] Field of Search ......................... 546/271; 514/341

[56] References Cited

PUBLICATIONS

Chem. Abstracts, vol. 45: 1116g, 1951.
Chem. Abstracts, vol. 98: 46775h, 1983.

Primary Examiner—Mary C. Lee
Assistant Examiner—Zinna Northington
Attorney, Agent, or Firm—Wenderoth, Lind & Ponack

[57] ABSTRACT 2-(4-pyridylaminomethyl)benzimidazole derivatives of the following general formula:

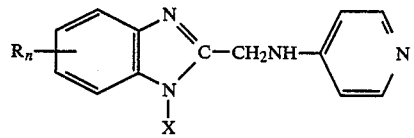

and processes for preparing them are described. The potent in vitro and in vivo antipicornavirus activities of the compounds are demonstrated.

15 Claims, No Drawings

2-(4-PYRIDYLAMINOMETHYL)-BENZIMIDAZOLE DERIVATIVES HAVING ANTIVIRAL ACTIVITY

BACKGROUND OF THE INVENTION (a) Field of the invention

The present invention relates to 2-(4-pyridylaminomethyl)benzimidazole derivatives. These compounds exhibit antiviral activity. The compounds are particularly effective against enterovirus and rhinovirus which are the causative agents of several human diseases.

(b) Description of the prior art

Since the benzimidazole derivatives were reported to show antiviral activity by R. L. Thompson (The Journal of Immunology: Vol. 55, 345 (1947)), synthesis and biological evaluation of a large number of this series of compounds has been reported. Especially, 2-(anilinomethyl)benzimidazole represented by the following formula:

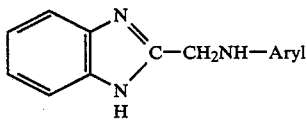

has been reported in Chemical Abstracts (Vol. 59, 3906f), and has been shown to exhibit biological activity (Mizuno et al.; Yakugaku Zasshi: Vol. 85, 926–955 (1965)).

The present inventors also newly synthesized the series of 2-(4-pyridylaminomethyl)benzimidazole derivatives represented by the following formula:

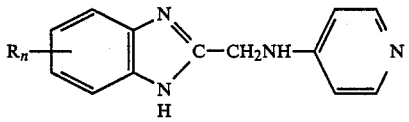

wherein n is 0, 1 or 2, R is lower alkyl, lower alkoxy, benzoyl, halogenomethyl, halogen, nitro or amino, their tautomers, and their acid addition salts, and these compounds were subjected to an antiviral activity test for primarily screening out promising ones (Japanese patent application No. 156,680/1985 dated July 15, 1985, which corresponds to U.S. patent application, Ser. No. 884,624 filed on July 11, 1986).

The picornaviruses are the causative agents of several disease states. Among the picornaviridae are two groups that cause disease in humans: the enteroviruses and the rhinoviruses. The enterovirus group consists of 68 distinct serotypes that have been associated with many diverse disease states, including poliomyelitis, neonatal sepsis, aseptic meningitis, pericarditis, myocarditis, hepatitis, eruption, acute hemorrhagic conjunctivitis and upper respiratory tract infections. Rhinoviruses have been shown to be important causative agents for the common cold. The widespread nature of picornavirus disease, the economic consequences, and impracticality of vaccine development have justified the search for chemotherapeutic agents.

DETAILED DESCRIPTION OF THE INVENTION

This invention provides novel 2-(4-pyridylaminomethyl)benzimidazole derivatives which have more expanded or increased kinds of substituents than those compounds in our former invention, as disclosed in U.S. patent application, Ser. No. 884,624 filed July 11, 1986.

It is one object of this invention to provide novel 2-(4-pyridylaminomethyl)benzimidazole derivatives and their acid addition salts. It is a further object of the invention to provide pharmaceutical compositions having antiviral activity, in particular antipicornavirus activity.

Preliminarily explaining the numbering of the benzimidazole ring:

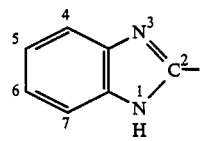

$N^1$ has a tautomer relation with $N^3$, and $C^5$ has the same relation with $C^6$, and $C^4$ has the same relation with $C^7$. Consequently, it is permitted to express any substituent located e.g. on the 5-position of the foregoing ring as 5 (6), and such expression will be followed in this specification.

The compounds of this invention are represented by the following general formula (I):

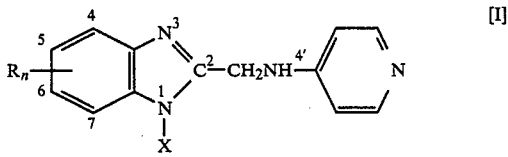

[I]

wherein X is selected from the group consisting of H, alkyl, alkenyl, cycloalkyl, hydroxyalkyl, mono- and dihalogeno-substitued phenyl, phenyl, mono-, di- and tri-alkyl-substituted phenyl, alkoxy-substitued phenyl, aralkyl, 3,3-dimethyl-2-oxobutyl, ethoxyethyl, 2-acetoxyethoxymethyl, trifluoromethylphenyl, 3-fluoro-4-tolyl and thiazolyl. n represents 0, 1 or 2 and R is selected from the group consisting of H, alkyl, phenyl, halogen, alkoxy and phenoxy groups.

More particularly, X can be a hydrogen atom, methyl, ethyl, n- and iso-propyl, propylenyl, n- and iso-butyl, iso-amyl, n-pentyl, cyclopentyl, n-hexyl, n-octyl, 2-hydroxyethyl, phenyl, p-tolyl, p-fluorophenyl, benzyl, 3-hydroxypropyl, 4-hydroxybutyl, 3,3-dimethyl-2-oxobutyl, ethoxyethyl, 2-acetoxyethoxymethyl, 3-phenylpropyl, o- and m-fluorophenyl, p-chlorophenyl, p-bromophenyl, p-iodophenyl, o- and m-tolyl, p-trifluoromethylphenyl, o- and p-ethylphenyl, o- and p-methoxyphenyl, 3,4-dichlorophenyl, 3,4-xylyl, 3-fluoro-4-tolyl, 2,4,6-trimethylphenyl, and 2-thiazolyl groups. R can be a hydrogen atom, -5(6)-substituted bromo, -fluoro, -iodo, -ethoxy, -n-propyl, -iso-propyl, -n- and -t-butyl and -phenyl, 4(7)-methyl-6(5)-chloro, 4(7)-chloro-6-(5)-methyl, 4(7)-chloro-6-(5)-chloro, 5(6)-methyl-6(5)-bromo, 5(6)-methyl-6(5)-chloro, 5(6)-methyl-6(5)-fluoro, 5(6)-ethyl-6(5)-bromo, 5(6)-ethyl-6(5)-chloro, 5(6)-methoxy-6(5)-chloro, 5,6-dimethoxy, 5(6)-fluoro-6(5)-chloro, 5-substituted-chloro, -methyl, -ethyl and -fluoro, 5(6)-substituted phenoxy and 5-chloro-6-ethyl groups.

Of the above-indicated compounds of this invention, those which have been identified by means of the underexplained in vivo and/or in vitro biological experiments to show more or less favourable antiviral activity will be listed together with their melting point in the following tables:

TABLE I

| Compound No. | Substituents X | R | Molecular Formula | Melting Pt. (°C.) |
|---|---|---|---|---|
| I | H | 5(6)-Br | $C_{13}H_{11}N_4Br.2HCl.\frac{1}{2}H_2O$ | 190 |
| II | H | 5(6)-F | $C_{13}H_{11}N_4F.2HCl.2H_2O$ | 195–198 |
| III | H | 5(6)-I | $C_{13}H_{11}N_4I.2HCl.H_2O$ | 199–203 |
| IV | H | 5(6)-OC$_2$H$_5$ | $C_{15}H_{16}N_4O.2HCl.H_2O$ | 177–180 |
| V | H | 5(6)-n-C$_3$H$_7$ | $C_{16}H_{18}N_4.2HCl.\frac{1}{2}H_2O$ | 186–190 |
| VI | H | 5(6)-i-C$_3$H$_7$ | $C_{16}H_{18}N_4.2HCl.3H_2O$ | 125–128 |
| VII | H | 5(6)-n-C$_4$H$_9$ | $C_{17}H_{20}N_4.2HCl.H_2O$ | 146–150 |
| VIII | H | 5(6)-t-C$_4$H$_9$ | $C_{17}H_{20}N_4.2HCl.\frac{1}{2}H_2O$ | 189–192 |
| IX | H | 5(6)-C$_6$H$_5$ | $C_{19}H_{16}N_4.2HCl.\frac{1}{2}H_2O$ | 190–193 |
| X | CH$_3$ | H | $C_{14}H_{14}N_4.HCl.3/2H_2O$ | 298–300 |
| XI | C$_2$H$_5$ | H | $C_{15}H_{16}N_4.HCl.\frac{1}{2}H_2O$ | 279–283 |
| XII | n-C$_3$H$_7$ | H | $C_{16}H_{18}N_4.HCl.\frac{1}{2}H_2O$ | 297–299 |
| XIII | i-C$_3$H$_7$ | H | $C_{16}H_{18}N_4.HCl.\frac{1}{2}H_2O$ | >300 |
| XIV | CH=CHCH$_3$ | H | $C_{16}H_{16}N_4.HCl.H_2O$ | 274–276 |
| XV | n-C$_4$H$_9$ | H | $C_{17}H_{20}N_4.HCl$ | 265–267 |
| XVI | n-C$_5$H$_{11}$ | H | $C_{18}H_{22}N_4.HCl.H_2O$ | 263–264 |
| XVII | cyclo-C$_5$H$_9$ | H | $C_{18}H_{20}N_4.NCl.H_2O$ | >300 |
| XVIII | n-C$_6$H$_{13}$ | H | $C_{19}H_{24}N_4.HCl.H_2O$ | 263–266 |
| XIX | n-C$_8$H$_{17}$ | H | $C_{21}H_{28}N_4.HCl.H_2O$ | 204–206 |
| XX | C$_2$H$_4$OH | H | $C_{15}H_{16}N_4O.HCl$ | 233–236 |
| XXI | C$_6$H$_5$ | H | $C_{19}H_{16}N_4.HCl.H_2O$ | >300 |
| XXII | p-C$_6$H$_4$CH$_3$ | H | $C_{20}H_{18}N_4.HCl.H_2O$ | >300 |
| XXIII | p-C$_6$H$_4$F | H | $C_{19}H_{15}N_4F.HCl.H_2O$ | 294–296 |
| XXIV | CH$_2$C$_6$H$_5$ | H | $C_{20}H_{18}N_4.HCl.\frac{1}{2}H_2O$ | 299–302 |
| XXV | H | 4(7)-CH$_3$ 6(5)-Cl | $C_{14}H_{13}N_4Cl.2HCl.2H_2O$ | 289–292 |
| XXVI | H | 4(7)-Cl 6(5)-CH$_3$ | $C_{14}H_{13}N_4Cl.2HCl.2H_2O$ | 210 |
| XXVII | H | 4(7)-Cl 6(5)-Cl | $C_{13}H_{10}N_4Cl_2.2HCl.H_2O$ | 172–175 |
| XXVIII | H | 5(6)-CH$_3$ 6(5)-Br | $C_{14}H_{13}N_4Br.2HCl$ | 279–282 |
| XXIX | H | 5(6)-CH$_3$ 6(5)-Cl | $C_{14}H_{13}N_4Cl.2HCl.H_2O$ | 288–292 |
| XXX | H | 5(6)-CH$_3$ 6(5)-F | $C_{14}H_{13}N_4F.2HCl.H_2O$ | 230–233 |
| XXXI | H | 5(6)-C$_2$H$_5$ 6(5)-Br | $C_{15}H_{15}N_4Br.2HCl$ | 208–212 |
| XXXII | H | 5(6)-C$_2$H$_5$ 6(5)-Cl | $C_{15}H_{15}N_4Cl.2HCl$ | 183–187 |
| XXXIII | H | 5(6)-OCH$_3$ 6(5)-Cl | $C_{14}H_{13}N_4OCl.2HCl.H_2O$ | 277–281 |
| XXXIV | H | 5(6)-OCH$_3$ 6(5)-OCH$_3$ | $C_{15}H_{16}N_4O_2.2HCl.2H_2O$ | 192–197 |
| XXXV | H | 5(6)-F 6(5)-Cl | $C_{13}H_{10}N_4FCl.2HCl$ | 173–176 |
| XXXVI | CH$_3$ | 5-CH$_3$ | $C_{15}H_{16}N_4.HCl.H_2O$ | 275–277 |
| XXXVII | CH$_3$ | 5-C$_2$H$_5$ | $C_{16}H_{18}N_4HCl.H_2O$ | 220–223 |
| XXXVIII | CH$_3$ | 5-Cl | $C_{14}H_{13}N_4Cl.HCl.\frac{1}{2}H_2O$ | 297–299 |
| XXXIX | CH$_3$ | 6-Cl | $C_{14}H_{13}N_4Cl.HCl.\frac{1}{2}H_2O$ | >300 |
| XL | C$_2$H$_5$ | 5-CH$_3$ | $C_{16}H_{18}N_4.HCl$ | 286–290 |
| XLI | C$_2$H$_5$ | 5-C$_2$H$_5$ | $C_{17}H_{20}N_4.HCl.H_2O$ | 300–303 |
| XLII | n-C$_4$H$_9$ | 5-CH$_3$ | $C_{18}H_{22}N_4.HCl.H_2O$ | 288–290 |
| XLIII | C$_6$H$_5$ | 6-CH$_3$ | $C_{20}H_{18}N_4.2HCl.2H_2O$ | 183 |
| XLIV | C$_6$H$_5$ | 5-C$_2$H$_5$ | $C_{21}H_{20}N_4.HCl$ | >300 |
| XLV | C$_6$H$_5$ | 6-C$_2$H$_5$ | $C_{21}H_{20}N_4.HCl$ | 255 |
| XLVI | C$_6$H$_5$ | 5-Cl | $C_{19}H_{15}N_4Cl.HCl.H_2O$ | 295–298 |
| XLVII | C$_6$H$_5$ | 6-Cl | $C_{19}H_{15}N_4Cl.HCl$ | >300 |
| XLVIII | C$_6$H$_5$ | 6-F | $C_{19}H_{15}N_4F.HCl$ | 296–299 |

TABLE II

| Compound No. | Substituents X | R | Molecular Formula | Melting Pt. (°C.) |
|---|---|---|---|---|
| XLIX | CH$_2$CH(CH$_3$)$_2$ | H | $C_{17}H_{20}N_4.HCl$ | >300 |
| L | CH$_2$CH$_2$CH(CH$_3$)$_2$ | H | $C_{18}H_{22}H_4.HCl.\frac{1}{2}H_2O$ | 261–264 |
| LI | n-(CH$_2$)$_3$OH | H | $C_{16}H_{18}N_4O.HCl$ | 270 (Dec.) |
| LII | n-(CH$_2$)$_4$OH | H | $C_{17}H_{20}H_4O.HCl.H_2O$ | 230–232 |
| LIII | CH$_2$COC(CH$_3$)$_3$ | H | $C_{19}H_{22}N_4O.2HCl.H_2O$ | 275–277 |
| LIV | CH$_2$CH$_2$OC$_2$H$_5$ | H | $C_{17}H_{20}N_4O.HCl$ | 249–251 |
| LV | CH$_2$OC$_2$H$_4$OCCH$_3$ $\parallel$ O | H | $C_{18}H_{20}N_4O_3.H_2O$ | Oily |

TABLE II-continued

| Compound No. | Substituents X | R | Molecular Formula | Melting Pt. (°C.) |
|---|---|---|---|---|
| LVI | $CH_2CH_2CH_2C_6H_5$ | H | $C_{22}H_{22}N_4.HCl$ | >300 |
| LVII | $o\text{-}C_6H_4F$ | H | $C_{19}H_{15}N_4F.HCl$ | 228–230 |
| LVIII | $m\text{-}C_6H_4F$ | H | $C_{19}H_{15}N_4F.HCl$ | >300 |
| LIX | $p\text{-}C_6H_4Cl$ | H | $C_{19}H_{15}N_4Cl.HCl$ | >300 |
| LX | $p\text{-}C_6H_4Br$ | H | $C_{19}H_{15}N_4Br.HCl$ | >300 |
| LXI | $p\text{-}C_6H_4I$ | H | $C_{19}H_{15}N_4I.HCl$ | >300 |
| LXII | $o\text{-}C_6H_4CH_3$ | H | $C_{20}H_{18}N_4.HCl.H_2O$ | 275–278 |
| LXIII | $m\text{-}C_6H_4CH_3$ | H | $C_{20}H_{18}N_4.HCl.H_2O$ | 241–244 |
| LXIV | $p\text{-}C_6H_4CF_3$ | H | $C_{20}H_{15}N_4F_3.HCl$ | >300 |
| LXV | $o\text{-}C_6H_4C_2H_5$ | H | $C_{21}H_{20}N_4.HCl$ | 305–310 |
| LXVI | $p\text{-}C_6H_4C_2H_5$ | H | $C_{21}H_{20}N_4.HCl$ | 298–301 |
| LXVII | $o\text{-}C_6H_4OCH_3$ | H | $C_{20}H_{18}N_4O.2HCl.H_2O$ | 255–260 |
| LXVIII | $p\text{-}C_6H_4OCH_3$ | H | $C_{20}H_{18}N_4O.HCl.H_2O$ | 260–262 |
| LXIX | $3,4\text{-di-ClC}_6H_3$ | H | $C_{19}H_{14}N_4Cl_2.HCl.H_2O$ | 222–226 |
| LXX | $3,4\text{-di-CH}_3C_6H_3$ | H | $C_{21}H_{20}N_4.HCl.H_2O$ | 165 |
| LXXI | $3\text{-F, }4\text{-CH}_3C_6H_3$ | H | $C_{20}H_{17}N_4F.HCl.H_2O$ | 280 (Dec.) |
| LXXII | $2,4,6\text{-tri-CH}_3C_6H_2$ | H | $C_{22}H_{22}N_4.HCl$ | 303–305 |
| LXXIII | (2-thiazolyl ring) | H | $C_{16}H_{13}N_5S.HCl.H_2O$ | 282–285 |
| LXXIV | H | $5(6)\text{-OC}_6H_5$ | $C_{19}H_{16}N_4O.2HCl$ | 195–199 |
| LXXV | $C_6H_5$ | $5\text{-Cl, }6\text{-C}_2H_5$ | $C_{12}H_{19}N_4Cl.HCl.\frac{1}{2}H_2O$ | >300 |

(Dec. = Decompose)

Representative examples of this invention are shown below:

EXAMPLES

EXAMPLE 1

Preparation of 2-(4-pyridylaminomethyl)-5-(6)-bromobenzimidazole (Compound No. I)

(a) Preparation of 4-bromo-o-phenylenediamine

A mixture of o-phenylenediamine (5 g, 46.2 mmol), acetic acid (40 ml) and acetic anhydride (10.4 g, 102 mmol) was cooled in ice water, to which a solution of bromine (8.9 g, 55.4 mmol) in acetic acid (10 ml) was added and the reaction mixture was stirred for 40 minutes at 50°–55° C. and then the mixture was poured into a solution of sodium hydrogensulfite (1.5 g) in ice water (300 ml).

The white precipitate was collected by filtration, washed with water and dried. The resulted crystal (5.8 g) and Claisen's alkali (20 ml) were heated for 30 minutes and hot water (30 ml) was added into the mixture. The mixture was heated for an additional 15 minutes and then cooled to 0°–5° C. The product was extracted with chloroform and washed with water. The organic layer was dried and concentrated in vacuo.

(b) Preparation of 2-chloromethyl-5(6)-bromobenzimidazole

To a solution of 4-bromo-o-phenylenediamine (1.5 g, 8 mmol) obtained in the preceding step (a) in hydrochloric acid (4N, 15 ml) was added monochloroacetic acid (1.13 g, 12 mmol) and refluxed for 3 hours. After cooling, the reaction solution was made slightly alkaline with aqueous ammonia and the oily product was extracted with ethyl acetate. The ethyl acetate layer was washed with water, dried and evaporated in vacuo. The residue was crystallized from petroleum ether.

(c) Preparation of 2-(4-pyridylaminomethyl)-5(6)-bromobenzimidazole.

A solution of 2-chloromethyl-5-bromobenzimidazole (0.7 g, 2.85 mmol) obtained in the preceding step (b) and 4-aminopyridine (0.4 g, 4.3 mmol) in ethanol (10 ml) was refluxed for 1 hour. The reaction solution was evaporated in vacuo. The residue was dissolved in water (20 ml) and washed several times with ethyl acetate (20 ml). The aqueous phase was evaporated in vacuo.

The residual oil was dissolved in concd. hydrochloric acid (1 ml), dried in vacuo and crystallized from ethanol. Recrystallization from methanol-acetone than gave the title compound (0.4 g, 1.0 mmol).

Analysis (%) for $C_{13}H_{11}N_4Br2HCl\frac{1}{2}H_2O$ Calcd: C, 40.12; H, 3.63; N, 14.11. Found: C, 40.54; H, 3.51; N, 14.55.

EXAMPLE 2

Preparation of 1-isopropyl-2-(4-pyridylaminomethyl)-benzimidazole hydrochloride (Compound No. XIII)

(a) Preparation of 1-isopropyl-2-chloromethylbenzimidazole

N-isopropyl-o-phenylenediamine (2.8 g, 18.6 mmol), which is a known compound, was reacted with monochloroacetic acid (2.64 g, 28 mmol) in hydrochloric acid. The reaction mixture was made to weak by alkaline alkali with aqueous ammonia and the obtained oily material was refined in a usual manner to give the title intermediate (2.5 g, 12 mmol).

(b) Preparation of Compound No. XIII 1-isopropyl-2-chloromethylbenzimidazole (2.5 g, 12 mmol) obtained in the preceding step (a) was reacted with 4-aminopyridine (2.3 g, 24 mmol) to produce the objective compound, which was crystallized from acetone and recrystallized from ethanol-acetone. The refined objective compound (1,2 g, 3.85 mmol) was obtained.

Analysis (%) for $C_{16}H_{18}N_4HCl.\frac{1}{2}H_2O$ Calcd.: C, 61.05; H, 6.38; N, 17.76. Found: C, 61.63; H, 6.47; N, 17.97.

EXAMPLE 3

Preparation of 1-benzyl-2-(4-pyridylaminomethyl)benzimidazole (Compound No. XXIV)

(a) Preparation of 1-benzyl-2-chloromethylbenzimidazole

N-benzyl-o-phenylenediamine (3 g, 15 mmol), which is a known compound, was added to polyphosphoric ester (10 g), to which monochloroacetic acid (1.1 g, 12 mmol) was added and heated at 120° C. for 1 hour. Then water was added to the mixture to decompose remaining polyphosphoric ester. The resultant was refined in a conventional process and the title intermediate (2.25 g, 8.8 mmol) was obtained.

(b) Preparation of Compound No. XXIV 1-benzyl-2-chloromethylbenzimidazole (2.25 g, 8.8 mmol) prepared in the preceding step (a) was mixed with 4-aminopyridine (1.65 g, 17.6 mmol) and they were refluxed for 2 hours in ethanol. The resultant was crystallized from acetone and recrystallized from ethanol, then the objective compound (1.0 g, 2.78 mmol) was obtained.

Analysis (%) for $C_{20}H_{18}N_4HCl.\frac{1}{2}H_2O$ Calcd.: C, 66.78; H, 5.48; N, 15.53. Found: C, 66.75; H, 5.60; N, 15.57.

EXAMPLE 4

Preparation of 2-(4-pyridylaminomethyl)-5(6)-ethyl-6(5)-bromobenzimidazole (Compound No. XXXI)

(a) Preparation of 4-ethyl-5-bromo-o-phenylenediamine 4-ethyl-o-phenylenediamine (2 g, 15 mmol), which is a known compound, was mixed with acetic acid (20 ml) and acetic anhydride (4 g, 40 mmol) under cooling, to which a cooled solution of bromine (3.2 g, 20 mmol) in acetic acid was added slowly. The mixed solution was added into a solution of sodium hydrogensulfite (1 g) in ice water (150 ml). The occurred precipitate was isolated, to which Claisen's alkali (12 ml) was added and refined in a conventional process.

(b) Preparation of 2-chloromethyl-5(6)-ethyl-6(5)-bromobenzimidazole

The product (2.7 g, 13 mmol) obtained in the preceding step (a), hydrochloric acid (4N, 15 ml) and monochloroacetic acid (1.8 g, 19 mmol) were refluxed for 2.5 hours and then the reaction mixture was made alkaline with aqueous ammonia. The occurred oily material was extracted with ethyl acetate and the product was treated as in a usual process to obtain the titled intermediate (1.9 g, 6 mmol).

(c) Preparation of 2-(4-pyridylaminomethyl)-5(6)-ethyl-6-(5)-bromobenzimidazole hydrochloride A solution of the product (1.9 g, 6 mmol) obtained in the preceding step (b) and 4-aminopyridine (1.1 g, 12 mmol) dissolved in ethanol (15 ml) was refluxed for 3 hours. After cooling, the reaction mixture was concentrated in vacuo and treated in turn with water, ethyl acetate and concd. hydrochloric acid then crystallized from ethanol. The objective compound (0.25 g, 0.62 mmol) was obtained.

Analysis (%) for $C_{15}H_{15}N_4Br.2HCl$ Calcd.: C, 46.26; H, 4.54; N, 14.32. Found: C, 44.58; H, 4.24; N, 13.86.

EXAMPLE 5

Preparation of 1-ethyl-2-(4-pyridylaminomethyl)-5-methyl benzimidazole (Compound No. XL)

(a) Preparation of 1-ethyl-2-chloromethyl-5-methyl benzimidazole 2-amino-4-methyl-N-ethylaniline (2.15 g, 14 mmol), which is a known compound, hydrochloric acid (4N, 15 ml) and monochloroacetic acid (2 g, 21 mmol) were refluxed for 2.5 hours. After cooling, the reactant was neutralized with ammonia. The occurred oily substance was extracted with ethyl acetate and the product was treated as in a usual process to obtain the title intermediate (1.0 g, 3.9 mmol).

(b) Preparation of 1-ethyl-2-(4-pyridylaminomethyl)-5-methylbenzimidazole hydrochloride The intermediate (1.0 g, 3.9 mmol) obtained in the preceding step (a) was dissolved in ethanol (10 ml) together with 4-aminopyridine (0.73 g, 7.8 mmol) and refluxed for 2 hours. The occurred material was crystallized from acetone and recrystallized from methanol-acetone, then the objective compound (0.6 g, 2.0 mmol) was obtained.

Analysis (%) for $C_{16}H_{18}N_4.HCl$ Calcd.: C, 62.19; H, 6.48; N, 18.09. Found: C, 63.46; H, 6.32; N, 18.50.

EXAMPLE 6

Preparation of 1-isoamyl-2-(4-pyridylaminomethyl)benzimidazole hydrochloride (Compound No. L)

(a) Preparation of N-isoamyl-o-phenylenediamine

Under cooling, o-nitroacetoanilide (7.2 g, 40 mmol), acetone (28 ml) and powdered potassium hydroxide (2.2 g, 39 mmol) were mixed, to which 1-bromo-3-methylbutane (6.0 g, 40 mmol) was added. After the mixture was refluxed for 5 hours, the precipitate was removed by filtration. The filtrate was concentrated in vacuo and was extracted with chloroform. The occurred oily substance (9.8 g, 39 mmol) was refluxed for concd. hydrochloric acid (39 ml, 390 mmol) for 3 hours. The resultant was extracted with chloroform and concentrated in vacuo to give oily substance (6.4 g, 30.7 mmol), which was added to a mixture of powdered iron (17.1 g, 306 mmol), ethanol (24.5 ml), water (6.2 ml) and concd. hydrochloric acid (0.3 ml, 300 mmol). After the mixture was refluxed for 1.5 hours, the product was treated as in a usual process to obtain the title intermediate.

(b) Preparation of 1-isoamyl-2-chloromethylbenzimidazole

N-isoamyl-o-phenylenediamine (3.5 g, 19.7 mmol) obtained in the preceding step (a), a hydrochloric acid (4N, 20 ml) and monochloroacetic acid (2.8 g, 29.6 mmol) were refluxed for 2 hours, then the reactant was made weakly alkaline with aqueous ammonia and the occurred oily substance was extracted with ethyl acetate.

(c) Preparation of 1-isoamyl-2-(4-pyridylaminomethyl)benzimidazole hydrochloride 1-isoamyl-2-chloromethylbenzimidazole (2.9 g, 12.2 mmol) prepared in the preceding step (b), 4-aminopyridine (3.9 g, 22.5 mmol) and ethanol (24 ml) were refluxed. After concentration of the reaction mixture in vacuo, the product was crystallized from acetone (2.9 g, 9.0 mmol) and recrystallized from ethanol, than the objective compound (1.5 g, 4.5 mmol) was obtained.

Analysis (%) for $C_{18}H_{22}N_4HCl.\frac{1}{2}H_2O$ Calcd.: C, 63.05; H, 7.18; N, 16.57. Found: C, 63.60; H, 7.12; N, 16.48.

EXAMPLE 7

Preparation of 1-(3-fluorophenyl)-2-(4-pyridylaminomethyl)benzimidazole hydrochloride (Compound No. LVIII)

(a) Preparation of N-(3-fluorophenyl)-o-phenylenediamine o-nitroaniline (2.8 g, 20.3 mmol), potassium carbonate (0.9 g, 6.5 mmol), cuprous iodide (0.78 g, 4.1 mmol) and 1-bromo-3-fluorobenzene (15.4 g, 88.0 mmol) were refluxed for 24 hours at 165° C. The reactant was subjected to steam distillation and the remainder was extracted with ethyl acetate. The ethyl acetate layer was washed, dried and concentrated in vacuo. The obtained residue was refined by a silica gel column chromatography (CHCl₃). The eluent (1.2 g, 5.2 mmol) was refluxed for 1 hour together with powdered iron (2.9 g, 52 mmol), ethanol (4.2 ml), water (1 ml) and concd. hydrochloric acid (0.05 ml, 50 mmol), then the resultant was concentrated in vacuo.

(b) Preparation of 1-(3-fluorophenyl)-2-chloromethylbenzimidazole

A mixture of N-(3-fluorophenyl)-o-phenylenediamine (0.8 g, 4 mmol) prepared in the preceding step (a), polyphosphoric ester (2.7 g) and monochloroacetic acid (0.4 g, 4.2 mmol) was heated for 1 hour at 130° C. and water was added to the reaction mixture to decompose an excess of polyphosphoric ester, then neutralized with sodium carbonate and the occurred oily substance was extracted with chloroform and the extract was washed, dried and concentrated in vacuo.

(c) Preparation of 1-(3-fluorophenyl)-2-(4-pyridylaminomethyl)benzimidazole

A ethanol (8 ml) solution of 1-(3-fluorophenyl)-2-chloromethylbenzimidazole (1.0 g, 4 mmol) prepared in the preceding step (b) and 4-aminopyridine (1.3 g, 7.4 mmol) was refluxed for 1.5 hours. The reaction mixture was concentrated in vacuo and crystallized from acetone and recrystallized from ethanol-acetone, then the objective compound (0.3 g, 0.82 mmol) was obtained.

Analysis (%) for $C_{19}H_{15}N_4F \cdot HCl \cdot \frac{1}{2}H_2O$ Calcd.: C, 62.15; H, 5.04; N, 15.28. Found: C, 62.72; H, 4.71; N, 15.40.

EXAMPLE 8

Preparation of 1-phenyl-2-(4-pyridylaminomethyl)-5-chloro-6-ethylbenzimidazole (Compound No. LXXV)

(a) Preparation of 2-anilino-4-ethyl-5-chloroaniline

Under cooling, to a mixture of 3-ethylaniline (4.7 g, 39 mmol) and acetic anhydride (21.6 g, 212 mmol) was added nitric acid (70%, 5.5 ml) dropwise and continued with stirring for 1 hour at room temperature. The resultant was poured into ice water and the oily product was extracted with chloroform and the extract was washed with water, a water solution of sodium hydrogencarbonate, and water, dried and was concentrated in vacuo. Chlorine gas was introduced into an acetic acid (33 ml) solution of the concentrated material under cooling with ice, into which a water (210 ml) solution of sodium hydrogensulfite (2.1 g) was added under stirring for 3 hours at 35°–45° C. The occurred oily precipitate was extracted with chloroform and the extract was washed, dried and concentrated in vacuo, to which Claisen's alkali (20 ml) was added and the mixture was heated for 15 minutes, then hot water (20 ml) was added thereto and heated again for 15 minutes, then they were cooled rapidly to produce a precipitate, which was dissolved in chloroform, washed, dried and concentrated in vacuo.

A mixture of the obtained oily substance (6.0 g, 30 mmol), potassium carbonate (1.4 g, 10 mmol), cuprous iodide (1.2 g, 6 mmol) and bromobenzene (23.6 g, 150 mmol) was refluxed for 24 hours at 165° C., then it was subjected to steam distillation. The remainder was added to ethyl acetate and the ethyl acetate layer was separated and washed, dried and concentrated in vacuo.

The concentrated substance was added to a mixture of powdered iron (10.1 g, 180 mmol), ethanol (15 ml), water (3.8 ml) and concd. hydrochloric acid (0.18 ml, 180 mmol) and was refluxed for 1.5 hours and the filtrate was concentrated in vacuo.

(b) Preparation of 1-phenyl-2-chloromethyl-5-chloro-6-ethylbenzimidazole

A mixture of 2-anilino-4-ethyl-5-chloroaniline (3.3 g, 13.4 mmol) prepared in the preceding step (a), polyphosphoric ester (8.9 g) and monochloroacetic acid (1.3 g, 13.4 mmol) was heated for 1 hour at 130° C. under stirring. Water was added to the reaction mixture to decompose an excess of the ester and they were neutralized with sodium carbonate and the occurred oily substance was extracted with chloroform, which was washed, dried, and concentrated in vacuo.

(c) Preparation of 1-phenyl-2-(4-pyridylaminomethyl)-5-chloro-6-ethylbenzimidazole hydrochloride A mixture of 1-phenyl-2-chloromethyl-5-chloro-6-ethylbenzimidazole (1.7 g, 5.5 mmol) prepared in the preceding step (b), 4-aminopyridine (1.8 g, 10.3 mmol) and ethanol (10.8 ml) was refluxed for 1.5 hours, then the mixture was filtered and the filtrate was concentrated in vacuo and crystallized from acetone (1.0 g, 2.35 mmol) and recrystallized from ethanol, then the objective compound (0.35 g, 0.82 mmol) was obtained.

Analysis (%) for $C_{21}H_{19}N_4Cl \cdot 3/2 H_2O$ Calcd.: C, 58.89; H, 4.84; N, 13.27. Found: C, 59.16; H, 5.44; N, 13.14.

The test results of antipicornavirus activity studies on the compounds of the invention are described in following Experiment 1 (in vitro antiviral activity) and Experiment 2 (in vivo antiviral activity).

EXPERIMENT 1

In vitro antiviral activity

Methods;

(a) Inhibition of human enterovirus and rhinovirus plaque formation.

For the virus plaque reduction assay, medium was aspirated from confluent monolayers of cells in a 60 mm plastic petri dish and infected with about 100 plaque-forming units (PFU) of the appropriate virus. The cultures were incubated for 1 hr at 37° C. for poliovirus type 2 (Polio2) and coxsackievirus type B4 (CB4) or 33° C. for rhinovirus type 14 (HRV14) and enterovirus type 70 (EV70). The virus inoculum was removed, and the cells were overlaid with Eagle MEM containing 0.9% agar and various concentrations of the compound to be tested. The overlay for HRV14 infected cells also contained 10 mM $MgCl_2$ and 50 μg of DEAE-dextran per ml. The cultures were incubated at 37° C. for Polio2 and CB4 and 33° C. for HRV14 and EV70 in a 5% $CO_2$ atmosphere. On the day plaques appeared, the second overlay was added with the same medium plus neutral red (0.009%) and plaques were counted. The concentration of the test compound necessary to reduce the number of plaques by 50% when compared to untreated controls was considered the $IC_{50}$. Enteroviruses were assayed in LLC-$MK_2$ cells; HRV14 was assayed in HeLa cells.

(b) Inhibition of viral cytopathogenic effect.

For the assay of cytopathogenic effect (CPE), cells were transferred to 96-well microtest plates at a concentration of $2.0 \times 10^4$ cells per well in 0.1 ml of growth medium. After 24 hr of growth at 37° C. in a humidified $CO_2$ (5% $CO_2$, 95% air) incubator, the cultures were 80% monolayered and ready for use. The cell cultures in the microtest plates were drained growth medium and were challenged with 20 μl (100–300 $TCID_{50}$) of virus. Cell cultures were incubated for 1 hr at 33° or 37° C. The virus inoculum was removed, and the cell cultures were then refed with 0.1 ml of MEM containing the test compound at various concentrations. The cultures were maintained at 33° or 36° C. in a humidified $CO_2$ incubator and examined microscopically at 48, 72, 96 and 120 hr after challenge for virus CPE. Polio2 and CB4 were assayed in LLC-MK$_2$ cells at 37° C.; EV70 was assayed in LLC-MK$_2$ cells at 33° C.; HRV14 was assayed in HeLa cells at 33° C. The lowest concentration of a compound that reduced virus CPE by 50% or more was considered to be the IC$_{50}$.

(c) Evaluation of cytotoxicity.

Cytotoxicity measurement was based on alteration of normal cell morphology. To evaluate cell morphology, confluent LLC-MK$_2$ and HaLa cell monolayers which had not been infected but were treated with various concentrations of the test compounds were incubated in parallel with the virus-infected cell cultures and examined microscopically at the same time as viral cytopathogenicity was recorded for the virus-infected cell cultures. Any change in cell morphology, e.g., rounding up, shrinking or detachment of the cells, was considered as evidence for cytotoxocity. The lowest concentration of a compound that caused morphological cytotoxicity by 50% or more when compared to the compound-free controls was considered the CD$_{50}$.

Results;

The test results of Experiment 1 as shown in Tables III and IV. Based on the IC$_{50}$ required to inhibit virus plaque formation or virus CPE and the cytotoxicity parameters (expressed as CD$_{50}$), chemotherapeutic indexes (CI) were calculated by the following formula:

$$CI = CD_{50}/IC_{50}$$

Some of the compounds tested exhibited a potent and highly selective antipicornavirus activity.

TABLE III

| Compound No. | IC$_{50}$ (μg/ml) (A) | | | (B) | CD$_{50}$ (μg/ml) (C) | (D) | CI (C)/(A) | | | (D)/(B) |
|---|---|---|---|---|---|---|---|---|---|---|
| | EV70 | Polio2 | CB4 | HRV14 | LIC-MK$_2$ | HeLa | EV70 | Polio2 | CB4 | HRV14 |
| I | 3.1 | >25.0 | 18.0 | 5.8 | 312.3 | 17.8 | 101 | | 17 | 3 |
| II | 1.4 | >25.0 | 6.0 | 14.5 | 176.8 | 56.2 | 126 | | 29 | 4 |
| III | 6.5 | >100.0 | 33.0 | 6.2 | >100.0 | | >15 | | >3 | |
| IV | 39.0 | 460.0 | 93.0 | >100.0* | >100.0 | >100.0 | >3 | | >1 | |
| V | 3.8 | >100.0 | >100.0 | | 353.6 | | 93 | | | |
| VI | 2.1 | >100.0 | 69.0 | 16.5 | >1,000.0 | 56.2 | >476 | | >15 | 3 |
| VII | 17.8 | | | | 56.2 | | 3 | | | |
| VIII | >100.0* | | | | >100.0 | | | | | |
| IX | >100.0* | | | | >100.0 | | | | | |
| X | 33.0 | 170.0 | 32.0 | >100.0 | >1,000.0 | | >30 | >6 | >31 | |
| XI | >100.0* | | 3.2 | | 5,656.9 | | | | 1,768 | |
| XII | 4.3 | 3.6 | 0.47 | >50.0 | >2,000.0 | | >465 | >556 | >4,255 | |
| XIII | >100.0* | | 85.0 | | >100.0 | | | | >1 | |
| XIV | >100.0* | | 56.2 | | >2,000.0 | | | | >36 | |
| XV | 1.4 | 3.2 | 0.37 | >50.0 | >2,000.0 | | >1,429 | >625 | >5,405 | |
| XVI | 2.2 | 19.0 | <0.50 | >50.0 | 1,414.1 | | 643 | 74 | >2,828 | |
| XVII | >100.0* | | 5.6* | >50.0 | 1,414.1 | | | | >253 | |
| XVIII | 44.0 | >100.0 | 1.3 | | 707.1 | | 16 | | 544 | |
| XIX | >100.0* | | 14.8 | | 353.6 | | | | 24 | |
| XX | >100.0* | | >100.0 | | >2,000.0 | | | | | |
| XXI | 1.5 | 48.0 | 1.5 | >50.0 | 1,414.1 | | 943 | 29 | 943 | |
| XXII | 0.52 | >10.0 | 0.48 | 38.0 | 1,414.1 | | 2,719 | | 2,946 | |
| XXIII | 1.1 | 7.8 | 0.83 | 30.0 | >2,000.0 | | >1,818 | >256 | >2,410 | |
| XXIV | >100.0* | | 56.2* | >50.0 | >2,000.0 | | | | >36 | |
| XXV | 56.2* | | | 17.8* | 707.1 | 17.8 | 13 | | | |
| XXVI | >100.0* | | | >56.2* | 1,414.1 | 56.2 | | | | |
| XXVII | >100.0* | | | >17.8* | >100.0 | 17.8 | | | | |
| XXVIII | 2.0 | 34.0 | 13.5 | 3.6 | 176.8 | 56.2 | 88 | 5 | 13 | 15 |
| XXIX | 1.5 | 52.0 | 11.5 | 3.8 | 176.8 | 56.2 | 118 | 3 | 15 | 15 |
| XXX | 12.0 | >100.0 | >50.0 | 8.6 | >100.0 | | >8 | | | |
| XXXI | 1.2 | 82.0 | >10.0 | 1.4 | 88.4 | | 74 | 1 | | |
| XXXII | 0.66 | 35.0 | 12.5 | <1.0 | 88.4 | | 134 | 3 | 7 | |
| XXXIII | 56.2* | | | | >100.0 | | >2 | | | |
| XXXIV | >100.0* | | | | >100.0 | | | | | |
| XXXV | 6.8 | >100.0 | 34.0 | 15.5 | >100.0 | | >15 | | >3 | |
| XXXVI | >100.0* | | | | >100.0 | | | | | |
| XXXVII | 22.0 | >100.0 | >50.0 | 20.0 | >100.0 | | >5 | | | |
| XXXVIII | 115.0 | >100.0 | 56.0 | >50.0 | >100.0 | | | | >2 | |
| XXXIX | 50.0 | >100.0 | 82.0 | >50.0 | >100.0 | | >2 | | >1 | |
| XL | >100.0* | | 56.2* | | >100.0 | | | | >2 | |
| XLI | >100.0* | | >100.0* | | >100.0 | | | | | |
| XLII | 5.9 | 27.6 | 1.4 | >50.0 | 1,414.1 | | 240 | 51 | 1,010 | |
| XLIII | 17.8* | | 3.2* | >100.0* | >100.0 | >100.0 | >6 | | >31 | |
| XLIV | 3.2* | | 6.8* | 17.8* | >100.0 | >100.0 | >31 | | >15 | >6 |
| XLV | 1.6 | >100.0 | 5.0 | 5.6* | 56.2 | 56.2 | 35 | | 11 | 10 |
| XLVI | 13.2* | | 1.8* | | >100.0 | | >8 | | >56 | |
| XLVII | 2.3 | >100.0 | 1.2 | 4.4 | >300.0 | 17.8 | >130 | | >250 | 4 |
| XLVIII | >100.0* | | >100.0* | | >100.0 | | | | | |

*Virus CPE inhibition assay

TABLE IV

| Compound No. | IC$_{50}$ (µg/ml) (A) EV70 | Polio2 | CB4 | (B) HRV14 | CD$_{50}$ (µg/ml) (C) LIC-MK$_2$ | (D) HeLa | CI (C)/(A) EV70 | Polio2 | CB4 | (D)/(B) HRV14 |
|---|---|---|---|---|---|---|---|---|---|---|
| XLIX | >100.0 | | 2.1* | >100.0* | >2,000 | | | | >952 | |
| L | 1.4 | 4.3 | 0.34 | >100.0 | 1,414.8 | | 1,010 | 329 | 4,159 | |
| LI | >100.0* | | 56.2* | >100.0 | >1,000 | | | | 18 | |
| LII | >100.0* | | 17.8* | | >100 | | | | >6 | |
| LIII | >100.0* | | >100.0* | >100.0* | >2,000 | | | | | |
| LIV | >100.0* | | >100.0* | >100.0* | >2,000 | | | | | |
| LV | 1.6 | 17.6 | 11.9 | 15.6 | >100 | >100 | >63 | >6 | 8 | >6 |
| LVI | >100.0* | | >100.0* | | >100 | | | | | |
| LVII | 24.1 | >100.0 | 8.6 | >100.0* | 2,000 | >100 | 83 | | 233 | |
| LVIII | 5.0 | >100.0 | 3.6 | >100.0* | >1,000 | >100 | >200 | | >278 | |
| LIX | 1.2 | 9.6 | 0.85 | 25.0 | >1,000 | >100 | >833 | >111 | >1,176 | >4 |
| LX | 1.9 | >50 | 1.0 | 39.9 | >100 | >100 | >53 | | >100 | >3 |
| LXI | >100.0* | | >100.0* | | >100 | | | | | |
| LXII | >100.0* | | >100.0* | | >100 | | | | | |
| LXIII | 5.6 | | 5.6* | | >100 | | >18 | | >18 | |
| LXIV | >100.0* | | 5.6* | | >100 | | | | >18 | |
| LXV | >100.0* | | >100.0* | >100.0* | >100 | >100 | | | | |
| LXVI | >100.0 | >100.0 | 2.7 | >100.0 | >100 | | | | >37 | |
| LXVII | >100.0* | | >100.0* | | | | | | | |
| LXVIII | >100.0* | | 5.6* | | >100 | | | | >18 | |
| LXIX | 5.6* | | 5.6* | | >100 | | >18 | | >18 | |
| LXX | 6.5 | >50 | 16.0 | 40.7 | >100 | >100 | >15 | | >6 | >2 |
| LXXI | 4.0 | >50 | 3.2 | 49.7 | >100 | >100 | >25 | | >31 | >2 |
| LXXII | >100.0* | | >100.0* | | >100 | | | | | |
| LXXIII | >100.0* | | >100.0* | >100.0* | >100 | >100 | | | | |
| LXXIV | >100.0* | | >100.0* | 17.8 | >100 | >100 | | | | >6 |
| LXXV | >56.2* | | >100.0* | 5.6* | >100 | 17.8 | >2 | | | 3 |

*Virus CPE inhibition assay

EXPERIMENT 2

Anti-coxsackievirus activity, in vivo.

Methods;

Compound No. XII and XXI were examined for its activity against CB4-induced hypoglycemia in SJL/J mice. Seven to eight week-old female SJL/J mice were infected intraperitoneally (i.p.) with $10^3$ PFU of CB4 strain 637. Infected micew were treated i.p. with 40 mg/kg of compounds at 1 and 19 hr after infection and with 80 mg/kg of compounds at 2, 5, 29, 48, 72 and 96 hr after infection. Blood specimens were collected from the tail vein of each mouse before and 2, 3, 4 and 5 days after infection for assaying its plasma glucose levels. The differences in mean relative plasma glucose of uninfected control and compound-treated groups or placebo groups were evaluated by Student's t-test.

Results;

The test results of Experiment 2 showed that both compounds significantly prevented the development of CB4-induced hypoglycemia 2 to 4 days after infection compared with the placebo. Therefore, the profiles of plasma glucose in mice treated with the compounds were normal level. This effect was associated with reductions in viral titers in the pancreas of infected animals relative to untreated, infected mice.

In addition, single, daily intraperitoneal doses of compound No. XII as low as 20 mg/kg (initiated 2 hr after infection and continued for 5 days) inhibited the onset of CB4-induced hypoglycemia.

Clinical application studies with some of compounds of this invention are in progress, however, they are expected to be as a drug for the prophylaxis and the treatment of picornavirus disease, which range from neonatal sepsis, aseptic meningitis and hepatitis A to the more common upper respiratory tract disease (colds).

Some of the compounds of this invention may be used in a variety of forms, such as tablet, capsule, syrups, an injection, suppository, ointment and eye lotion.

What we claim is:

1. A compound of the formula:

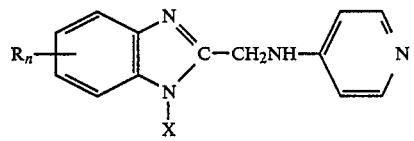

wherein X is selected from the group consisting of hydrogen, alkyl of 1-8 carbon atoms, propylenyl, cyclopentyl, hydroxyalkyl of 2-4 carbon atoms, phenyl, mono- and di-halogenophenyl, tolyl, xylyl, trimethylphenyl, ethylphenyl, methoxyphenyl, phenylalkyl of 1-3 carbon atoms in the alkyl group, 3,3-dimethyl-2-oxobutyl, ethoxyethyl, 2-acetoxyethoxymethyl, trifluoromethylphenyl, 3-fluoro-4-tolyl and thiazolyl, R is selected from the group consisting of hydrogen, halogen, methoxy, ethoxy, alkyl of 1-4 carbon atoms, phenyl and phenoxy, and n is an integer of 0, 1 or 2, or a pharmaceutically acceptable acid addition salt thereof, excluding the compounds where, when X is hydrogen, $R_n$ is hydrogen, 5(6)-chloro, 5(6)-methoxy, 5(6)-methyl, 5,6-dichloro, 5(6)-ethyl, 4(7)-methyl or 5,6-dimethyl.

2. A compound of the formula

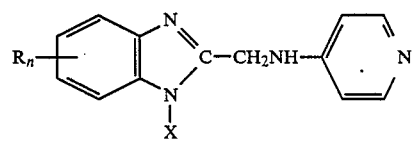

wherein X is selected from the group consisting of hydrogen, methyl, ethyl, n-propyl, iso-propyl, n-butyl, iso-butyl, n-pentyl, iso-amyl, n-hexyl, n-octyl, propylenyl, cyclopentyl, 2-hydroxyethyl, 3-hydroxypropyl, 4-hydroxybutyl, ethoxyethyl, 2-acetoxyethoxymethyl, 3,3-dimethyl-2-oxobutyl, benzyl, 3-phenylpropyl, phenyl, o-tolyl, m-tolyl, p-tolyl, o-ethylphenyl, p-ethylphenyl, p-trifluoromethylphenyl, o-fluorophenyl, m-fluorophenyl, p-fluorophenyl, p-chlorophenyl, p-bromophenyl, p-iodophenyl, o-methoxyphenyl, p-methoxyphenyl, 3,4-dichlorophenyl, 3,4-xylyl, 3-fluoro-4-tolyl, 2,4,6-trimethylphenyl and 2-thiazolyl, and $R_n$ is selected from the group consisting of hydrogen, 5(6)-methyl, 5(6)-ethyl, 5(6)-n-propyl, 5(6)-iso-propyl, 5(6)-n-butyl, 5(6)-t-butyl, 5(6)-ethoxy, 5(6)-chloro, 5(6)-bromo, 5(6)-fluoro, 5(6)-iodo, 5(6)-phenyl, 5,6-dimethoxy, 4(7),6(5)-dichloro, 4(7)-methyl-6-(5)-chloro, 4(7)-chloro-6(5-methyl, 5(6)-methyl-6(5)-bromo, 5(6)-methyl-6(5)-chloro, 5(6)-methyl-6(5)-fluoro, 5(6)-ethyl-6(5)-bromo, 5(6)-ethyl-6(5)-chloro, 5(6)-methoxy-6(5)-chloro and 5(6)-fluoro-6(5)-chloro, or a pharmaceutically acceptable acid addition salt thereof, excluding the compounds where, when X is hydrogen, $R_n$ is hydrogen, 5(6)-chloro, 5(6)-methoxy, 5(6)-methyl, 5,6-dichloro, 5(6)-ethyl, 4(7)-methyl or 5,6-dimethyl.

3. A compound according to claim 1, namely 2-(4-pyridylaminomethyl)-5(6)-bromobenzimidazole or an acid addition salt thereof.

4. A compound according to claim 1, namely 1-n-propyl-2-(4-pyridylaminomethyl)benzimidazole or an acid addition salt thereof.

5. A compound according to claim 1, namely 1-isopropyl-2-(4-pyridylaminomethyl)benzimidazole or an acid addition salt thereof.

6. A compound according to claim 1, namely 1-phenyl-2-(4-pyridylaminomethyl)benzimidazole or an acid addition salt thereof.

7. A compound according to claim 1, namely 1-benzyl-2-(4-pyridylaminomethyl)benzimidazole or an acid addition salt thereof.

8. A compound according to claim 1, namely 2-(4-pyridylaminomethyl)-5(6)-ethyl-6(5)-bromobenzimidazole or an acid addition salt thereof.

9. A compound according to claim 1, namely 1-ethyl-2-(4-pyridylaminomethyl)benzimidazole or an acid addition salt thereof.

10. A compound according to claim 1, namely 1-isoamyl-2-(4-pyridylaminomethyl)benzimidazole or an acid addition salt thereof.

11. A compound according to claim 1, namely 1-(3-fluorophenyl)-2-(4-pyridylaminomethyl)benzimidazole or an acid addition salt thereof.

12. A compound according to claim 1, namely 1-phenyl-2-(4-pyridylaminomethyl)-5-chloro-6-ethylbenzimidazole or an acid addition salt thereof.

13. A compound according to claim 1, namely 1-n-butyl-2-(4-pyridylaminomethyl)benzimidazole or an acid addition salt thereof.

14. A compound according to claim 1, namely 1-(4-fluorophenyl)-2-(4-pyridylaminomethyl)benzimidazole or an acid addition salt thereof.

15. A pharmaceutical composition having antiviral activity, which comprises an antiviral amount of a compound according to claim 1 as an active ingredient, and a pharmaceutically acceptable carrier therefor.

* * * * *